US012761299B2

(12) United States Patent
Ohishi et al.

(10) Patent No.: US 12,761,299 B2
(45) Date of Patent: Oct. 13, 2026

(54) RECEIVING COIL WITH COIL ELEMENT THAT RECEIVES A MAGNETIC RESONANCE SIGNAL HAVING A PLURALITY OF DIFFERENT FREQUENCIES

(71) Applicant: Canon Kabushiki Kaisha, Tokyo (JP)

(72) Inventors: Takafumi Ohishi, Yokohama (JP); Sadanori Tomiha, Nasushiobara (JP)

(73) Assignee: Canon Kabushiki Kaisha, Tokyo (JP)

( * ) Notice: Subject to any disclaimer, the term of this patent is extended or adjusted under 35 U.S.C. 154(b) by 737 days.

(21) Appl. No.: 18/191,261

(22) Filed: Mar. 28, 2023

(65) Prior Publication Data

US 2023/0314537 A1 Oct. 5, 2023

(30) Foreign Application Priority Data

Mar. 31, 2022 (JP) ................................ 2022-058945

(51) Int. Cl.

| | |
|---|---|
| ***G01R 33/34*** | (2006.01) |
| ***A61B 5/055*** | (2006.01) |
| ***G01R 33/341*** | (2006.01) |
| ***G01R 33/3415*** | (2006.01) |
| ***G01R 33/36*** | (2006.01) |
| ***G01R 33/38*** | (2006.01) |
| ***G01R 33/565*** | (2006.01) |

(52) U.S. Cl.

CPC . *G01R 33/34046* (2013.01); *G01R 33/34007* (2013.01); *G01R 33/341* (2013.01); *G01R 33/3415* (2013.01); *G01R 33/3635* (2013.01); *G01R 33/3806* (2013.01); *G01R 33/5659* (2013.01); *A61B 5/055* (2013.01); *G01R 33/3642* (2013.01)

(58) Field of Classification Search

CPC .......... G01R 33/34046; G01R 33/3635; G01R 33/3806; G01R 33/5659; G01R 33/3415; G01R 33/341; G01R 33/34007; G01R 33/3642; A61B 5/055

USPC .......................................................... 324/318

See application file for complete search history.

(56) References Cited

U.S. PATENT DOCUMENTS

| | | | |
|---|---|---|---|
| 4,792,759 | A | 12/1988 | Keren et al. |
| 6,771,071 | B1 | 8/2004 | Wright et al. |
| 8,593,141 | B1 | 11/2013 | Radparvar et al. |
| 8,618,799 | B1 | 12/2013 | Radparvar et al. |

(Continued)

FOREIGN PATENT DOCUMENTS

| | | | |
|---|---|---|---|
| DE | 10 2021 000 282 | A1 | 9/2021 |
| JP | 2009-542295 | A | 12/2009 |

(Continued)

OTHER PUBLICATIONS

Extended European Patent Application issued Aug. 23, 2023 in European Patent Application No. 23165234.8, 8 pages.

(Continued)

*Primary Examiner* — Raul J Rios Russo

(74) *Attorney, Agent, or Firm* — Oblon, McClelland, Maier & Neustadt, L.L.P.

(57) ABSTRACT

In one embodiment, a receiving coil includes at least one coil element that can simultaneously receive a plurality of magnetic resonance signals having different frequencies, wherein a resonance structure for the different frequencies is provided in a single plane in each of the at least one coil element.

20 Claims, 9 Drawing Sheets

(56) References Cited

U.S. PATENT DOCUMENTS

| | | | | |
|---|---|---|---|---|
| 9,261,573 | B1 | 2/2016 | Radparvar et al. | |
| 9,618,591 | B1 | 4/2017 | Radparvar et al. | |
| 10,509,084 | B1 | 12/2019 | Radparvar et al. | |
| 2010/0271022 | A1* | 10/2010 | Mitsui | G01R 33/3415 324/309 |
| 2010/0301862 | A1 | 12/2010 | Tropp et al. | |
| 2012/0286921 | A1 | 11/2012 | Wang et al. | |
| 2013/0314091 | A1 | 11/2013 | Otake et al. | |
| 2015/0168511 | A1* | 6/2015 | Jeong | G01R 33/3415 324/321 |
| 2016/0084926 | A1* | 3/2016 | Kim | G01R 33/34046 324/322 |
| 2016/0109541 | A1* | 4/2016 | Hayakawa | A61B 5/055 324/322 |
| 2017/0097399 | A1* | 4/2017 | Shiodera | A61B 5/055 |
| 2022/0155390 | A1 | 5/2022 | Gomes | |
| 2023/0078150 | A1 | 3/2023 | Hong et al. | |
| 2023/0109705 | A1 | 4/2023 | De Matos Gomes | |
| 2024/0230803 | A1* | 7/2024 | Sakakura | G01R 33/381 |

FOREIGN PATENT DOCUMENTS

| | | | |
|---|---|---|---|
| WO | WO 2012/111433 | A1 | 8/2012 |
| WO | WO 2020/172673 | A1 | 8/2020 |
| WO | WO 2020/198396 | A1 | 10/2020 |

OTHER PUBLICATIONS

Japanese Office Action issued Oct. 14, 2025 in Japanese Patent Application No. 2022-058945, 4 pgs.

* cited by examiner

A-A' CROSS-SECTION

RECEIVING COIL WITH COIL ELEMENT THAT RECEIVES A MAGNETIC RESONANCE SIGNAL HAVING A PLURALITY OF DIFFERENT FREQUENCIES

CROSS-REFERENCE TO RELATED APPLICATION

This application claims the benefit of priority of Japanese Patent Application No. 2022-058945, filed on Mar. 31, 2022, the entire contents of which are incorporated herein by reference.

TECHNICAL FIELD

Disclosed Embodiments relate to a receiving coil and a magnetic resonance imaging (MRI) apparatus.

BACKGROUND

An MRI apparatus is an imaging apparatus that magnetically excites nuclear spin of an object placed in a static magnetic field with a radio frequency (RF) signal having the Larmor frequency and reconstructs an image on the basis of magnetic resonance (MR) signals emitted from the object due to the excitation.

Many MRI apparatuses have a configuration called a gantry in which a cylindrical space called a bore is formed. Imaging of an object (for example, a patient) is performed in a state in which a table with the object lying thereon is moved into the cylindrical space. Inside the gantry, a cylindrical static magnetic field magnet, a cylindrical gradient coil, and a cylindrical transmitting/receiving coil (i.e., WB (Whole Body) coil) are housed. In many conventional MRI apparatuses of this type, the static magnetic field magnet, the gradient coil, and the transmitting/receiving coil are cylindrical, so an MRI apparatus of this type is hereinafter referred to as a cylindrical MRI apparatus.

In the cylindrical MRI apparatus, imaging is performed in the closed space in the bore, and thus, imaging may be difficult for some patients having claustrophobia, for example.

A type of an MRI apparatus has also been developed, in which a static magnetic field magnet, a gradient coil, and an RF coil are formed in a flat plate shape, and an object such as a patient is imaged in an open space formed by being sandwiched between two planar static magnetic field magnets. Hereinafter, an MRI apparatus having this type of structure is referred to as a planar open magnet MRI system or a planar open magnet MRI apparatus. In the planar open magnet MRI apparatus, imaging is performed in the open space, and thus, even a patient having claustrophobia can be imaged.

The cylindrical MRI apparatus is intended to image the object in a narrow region with highly-uniform magnetic field inside the bore. By contrast, in the planar open magnet MRI apparatus, the object is imaged in a relatively wide open space, and thus, the position of the object with respect to the static magnetic field magnets is not necessarily fixed. In other words, the static magnetic field strength changes within a certain range depending on the position of the object with respect to the static magnetic field magnets. For this reason, in the planar open magnet MRI apparatus, when an MR signal is received by a conventional single frequency receiving coil, the imageable region, i.e., FOV (Field of View) is limited to a considerably narrow range.

An MR signal receiving coil, in which a matching circuit is mounted to make the frequency variable, has also been proposed. However, since this MR signal receiving coil cannot simultaneously receive a plurality of MR signals having different frequencies, the FOV itself remains narrow.

DETAILED DESCRIPTION

Hereinbelow, embodiments of the present invention will be described by referring to the accompanying drawings.

In one embodiment, a receiving coil includes at least one coil element that can simultaneously receive a magnetic resonance (MR) signal having a plurality of different frequencies, wherein a resonance structure for the plurality of different frequencies is provided in a single plane in the at least one coil element.

(MRI Apparatus)

Figure 1:
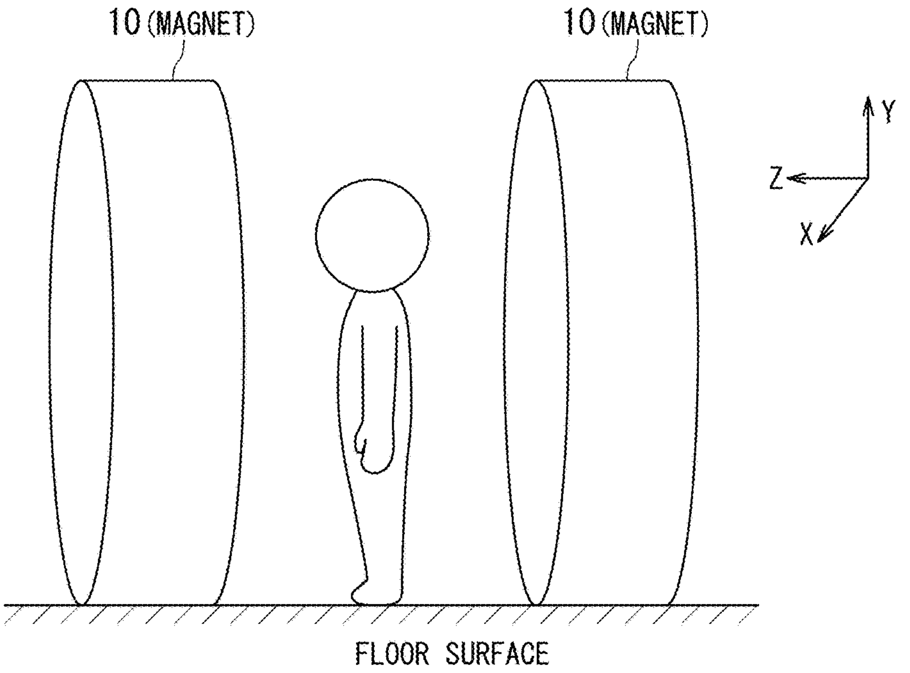
FIG. 1 is a schematic diagram illustrating a first configuration of an MRI apparatus according to one embodiment.

Of a first configuration of a planar open magnet MRI apparatus 1 according to the first embodiment, FIG. 1 particularly illustrates arrangement of static magnetic field magnets 10 (hereinafter shortly referred to as "the magnets 10"). As illustrated in FIG. 1, the MRI apparatus 1 has, for example, two magnets 10 in the shape of a circular flat plate (i.e., a pair of thin cylindrical magnets 10).

The respective magnets 10 are arranged such that the central axis of each magnet 10 (i.e., the axis passing through the center of the both circular end faces of the cylindrical shape) is parallel to, for example, the floor surface. In addition, the two magnets 10 are arranged so as to sandwich an object such as a patient. This arrangement of the magnets 10 generates a magnetic field in the open space between the two magnets 10. The object is imaged in this open space, for example, in a standing position.

When each magnet 10 is configured by using a superconducting coil, a static magnetic field is generated by applying a current supplied from a static magnetic field power supply to the superconducting coil in an excitation mode. Afterward, when each magnet 10 shifts to a permanent current mode, the static magnetic field power supply is disconnected and each magnet 10 continues to generate a magnetic field of constant strength. Each magnet 10 can also be configured as a permanent magnet.

Figure 2:
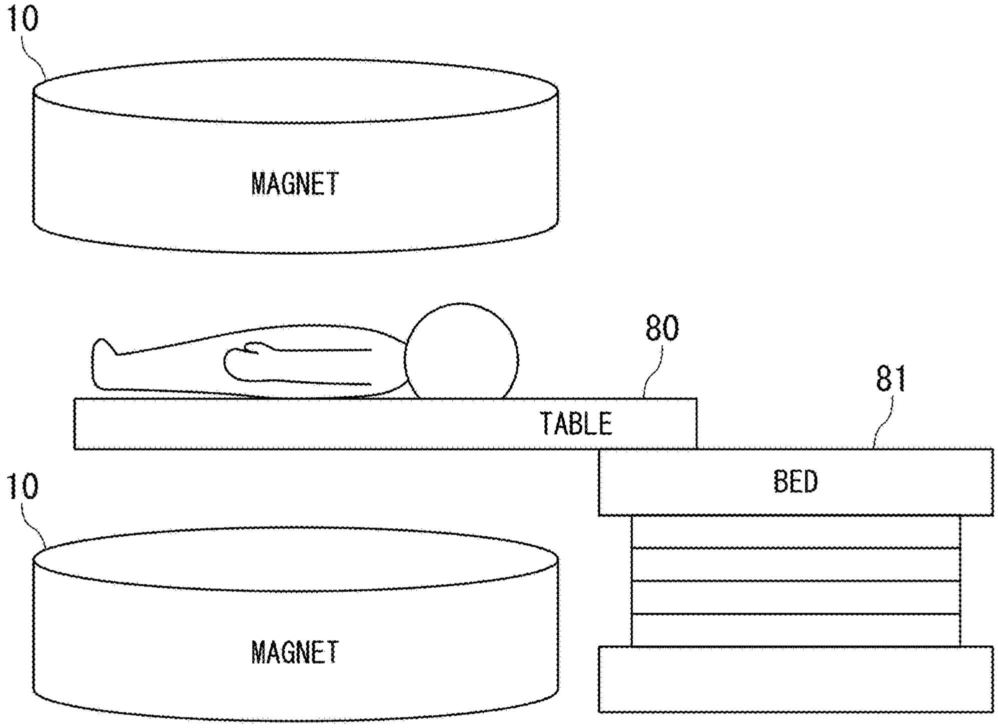
FIG. 2 is a schematic diagram illustrating a second configuration of the MRI apparatus according to the embodiment.

Of a second configuration of the planar open magnet MRI apparatus 1 according to the first embodiment, FIG. 2 particularly illustrates arrangement of the magnets 10. FIG. 1 illustrates a configuration for imaging an object in a standing position, whereas FIG. 2 illustrates a configuration for imaging an object in a lying position, i.e., lying on a table 80 extending from a bed 81. In the case of imaging the object in the lying position, the two magnets 10 are arranged such that their central axes are in the vertical direction as shown in FIG. 2. For example, one magnet 10 is disposed below the table 80 and the other magnet 10 is disposed above the table 80.

As shown in FIG. 1 and FIG. 2, when imaging by using the magnets 10 of the present embodiment, the object can be imaged in an open magnetic field space, and thus, even a patient having claustrophobia can be imaged, for example.

Figure 3B:
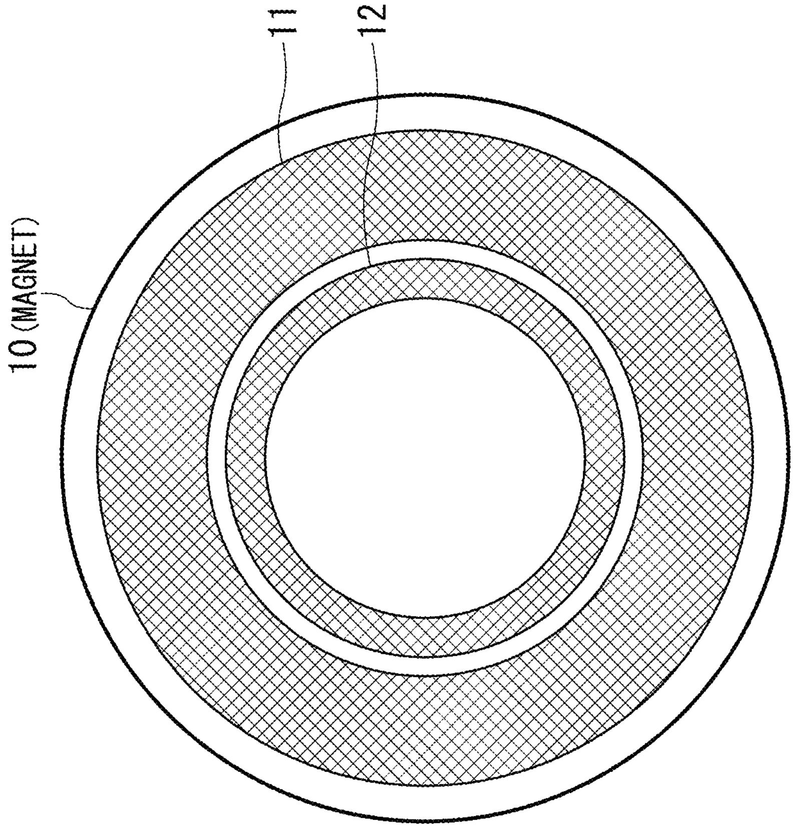
FIG. 3A and FIG. 3B are schematic diagrams illustrating an internal configuration of a static magnetic field magnet.
Figure 3A:
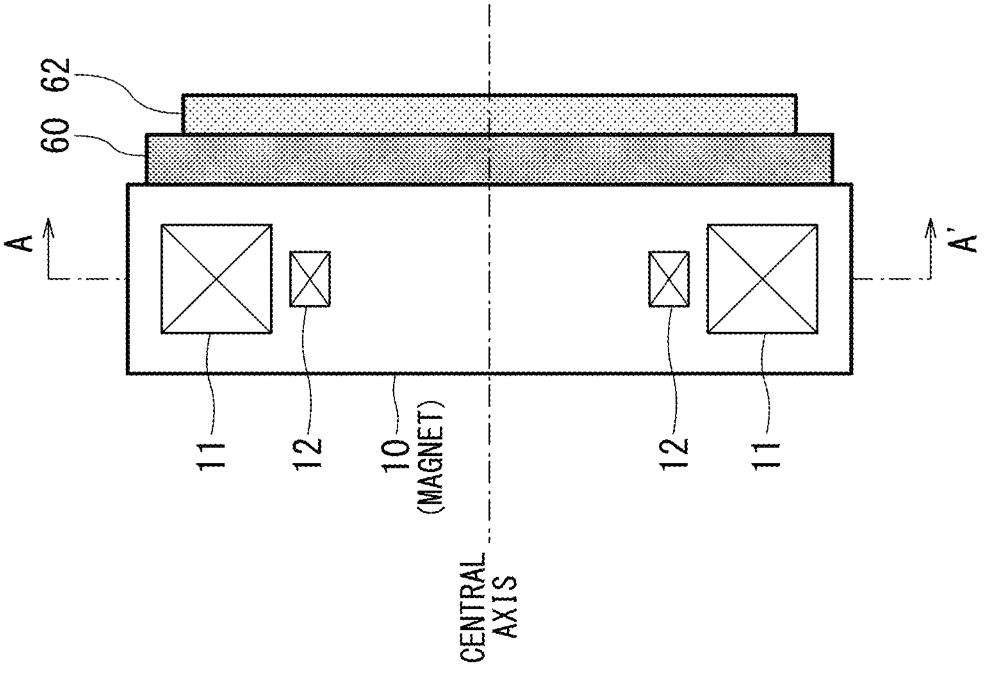

FIG. 3A and FIG. 3B are schematic diagrams illustrating the internal configuration of each magnet 10. FIG. 3A illustrates an internal cross-section of the magnet 10 as viewed from the direction orthogonal to the central axis. FIG. 3B is a cross-sectional view taken along the line A-A' of FIG. 3A for illustrating an internal cross-section of the magnet 10 as viewed from the central axis direction.

The magnets 10 are composed of one or more coil units, and the one or more coil units are housed in, for example, a flat plate-shaped magnet-housing that has a predetermined thickness as shown in FIG. 3A and FIG. 3B. In the case shown in FIG. 3A and FIG. 3B, for example, two circular coil units (i.e., coil units 11 and 12) having different cross-sectional areas are housed in the magnet-housing. The coil units 11 and 12 generate a static magnetic field that determines the magnetic resonance frequency.

Adjacent to the magnet-housing, a gradient coil assembly 60 and a transmitting coil 62 are disposed. The gradient coil assembly 60 generates a gradient magnetic field to be superimposed on the static magnetic field and is configured as, for example, a flat plate-shaped coil. The transmitting coil 62 applies a radio frequency (RF) pulse to the object and is also configured as, for example, a flat plate-shaped coil.

Figure 4:
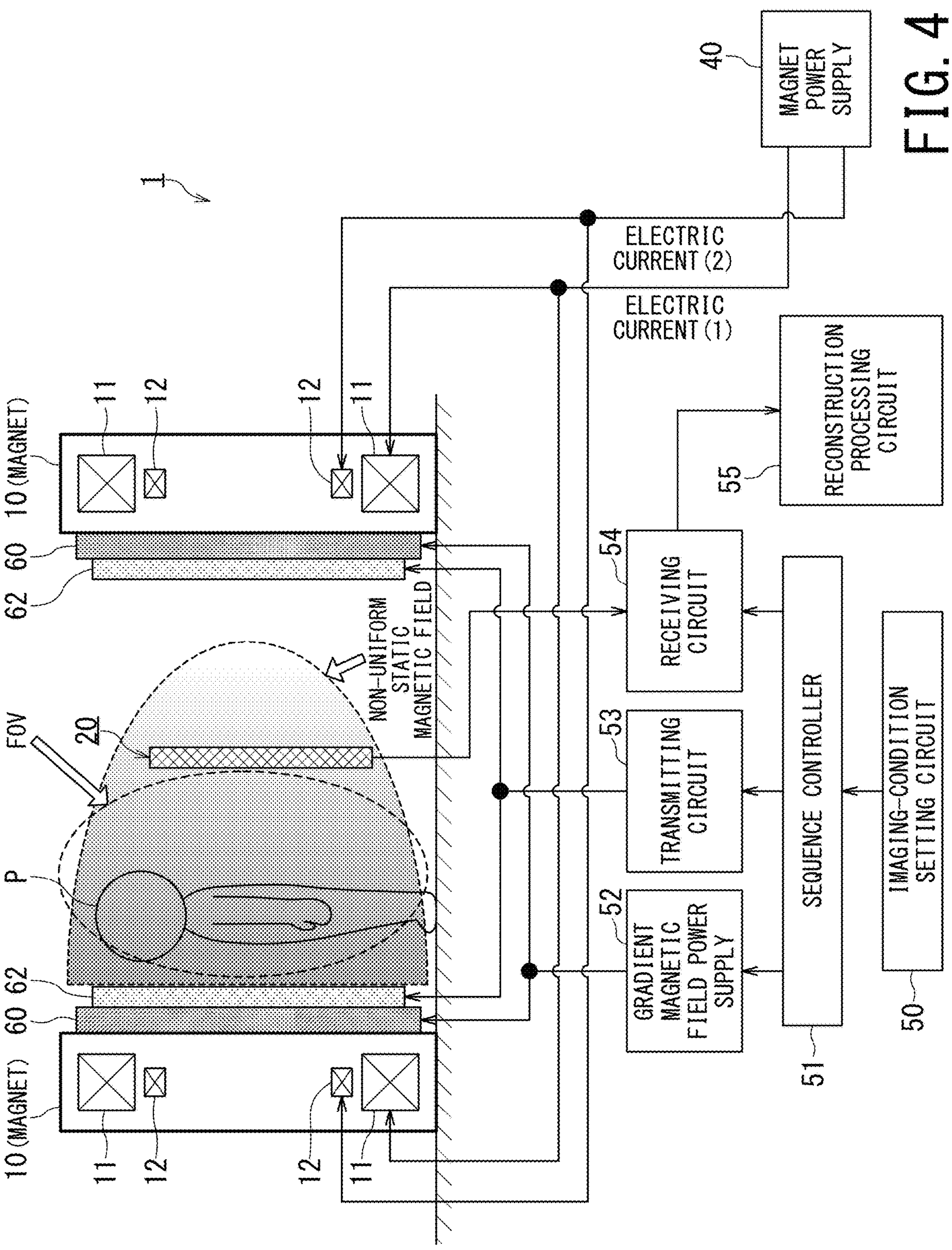
FIG. 4 is a block diagram illustrating a configuration of the MRI apparatus.

FIG. 4 is a block diagram illustrating a configuration of the MRI apparatus 1. This MRI apparatus 1 is provided with two magnet units, each of which includes: the magnet 10 shown in FIG. 3A and FIG. 3B; the gradient coil assembly 60; and the transmitting coil 62. The two magnet units are arranged so as to face each other with the object P interposed therebetween.

Further, in the MRI apparatus 1 as shown in FIG. 4, a receiving coil 20 is disposed at a position a little away from the left magnet units between which the object P is interposed. An imaging space (or FOV (Field of View)) is formed between the left magnet unit and the receiving coil 20.

When an excitation pulse transmitted from the transmitting coil 62 is applied to the object P, an MR signal is emitted from the object P in response to the application of this excitation pulse. This MR signal is received by the receiving coil 20. The receiving coil 20 is configured as, for example, a planar receiving antenna that extends in the direction perpendicular to the sheet of FIG. 4.

In the planar open magnet MRI apparatus 1, since the object P is imaged in a relatively wide opened space as described above, the position of the object P with respect to the magnets 10 is not necessarily fixed. That is, depending on the position of object P with respect to the magnets 10, the static magnetic field strength varies within a certain range. In other words, the object P is imaged while placed in a non-uniform static magnetic field.

Normally, the static magnetic field strength is stronger at a position closer to the magnet 10. As is well known, the magnetic resonance frequency is proportional to the static magnetic field strength. Thus, the closer the object P is to the magnet 10, the higher the magnetic resonance frequency becomes. Conversely, the farther the object P is from the magnet 10, the lower the magnetic resonance frequency becomes.

For this reason, when an MR signal is received by a conventional single-frequency receiving coil in a planar open magnet MRI apparatus, the imageable region, i.e., the FOV (Field of View) is limited to a considerably narrow range.

In view of the above-described problem, the receiving coil 20 of each embodiment ensures a wide FOV by broadening the frequency characteristics as described below.

In addition to the above-described magnet units and the receiving coil 20, the MRI apparatus 1 further includes: a magnet power supply 40; an imaging-condition setting circuit 50; a sequence controller 51; a gradient magnetic field power supply 52; a transmitting circuit 53; a receiving circuit 54; and a reconstruction processing circuit 55.

The magnet power supply 40 is configured to apply electric currents to the respective two coil units 11 and 12 of the magnets 10.

The imaging-condition setting circuit 50 is configured to set imaging conditions, such as the type of pulse sequence and the values of various parameters inputted via a user interface (not shown), to the sequence controller 51.

The sequence controller 53 is configured to perform a scan of the object by driving the gradient magnetic field power supply 52 and the transmitting circuit 53 based on the determined imaging conditions. The gradient magnetic field power supply 52 applies a gradient-magnetic-field current to the gradient coil assembly 60 based on a control signal from the sequence controller 51.

The transmitting circuit 53 is configured to generate an RF pulse based on the control signal from the sequence controller 51, and apply the RF pulse to the transmitting coil 62. The receiving coil 20 is configured to receive an MR signal emitted from the object P in response to the application of the RF pulse. The MR signal received by the receiving coil 20 is converted from an analog signal to a digital signal by the receiving circuit 54. The MR signal converted into the digital signal is inputted as k-space data into the reconstruction processing circuit 55. The reconstruction processing circuit 55 performs reconstruction processing such as inverse Fourier transform on the k-space data to generate a magnetic resonance image.

(Receiving Coil)

Hereinbelow, a description will be given of various embodiments of the receiving coil 20 to be used in the MRI apparatus 1.

The receiving coil 20 includes a plurality of coil elements. In each coil element as described below, a resonance structure for a plurality of frequencies is provided in a single plane, and thus, each coil element can simultaneously receive a plurality of MR signals having different frequencies. The receiving coil 20 is generally configured as an array coil in which the plurality of coil elements are arranged in the same plane as the above-described single plane. Note that the receiving coil 20 may be configured to have only one coil element.

As described above, the MR signal, which is received by the coil element, is emitted from the object in response to an excitation pulse that is applied to the object placed in a static magnetic field having non-uniform static magnetic field distribution. Note that the MR signal has different frequencies depending on the position of the object in the static magnetic field.

First Embodiment

Figure 5A:
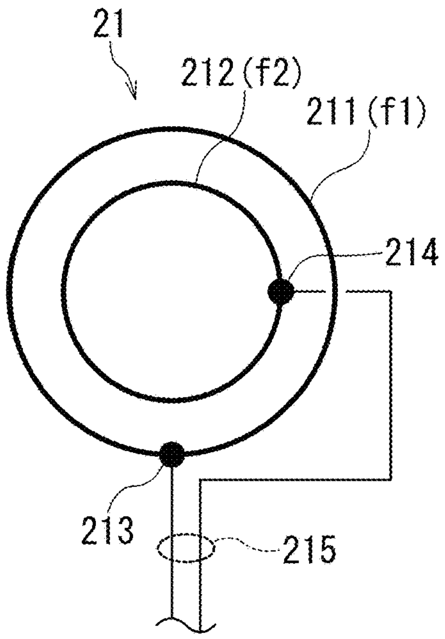
FIG. 5A is a configuration diagram illustrating a coil element according to the first embodiment.

FIG. 5A is a configuration diagram illustrating a coil element 21 according to the first embodiment. The coil element 21 is configured by arranging a plurality of loop coils in a single plane. Each of these loop coils resonates at each of different frequencies. These loop coils are different in diameter from each other and are supplied with electric power from respective different feeding points.

Although the number of the loop coils is not limited to a specific number, FIG. 5A particularly shows the configuration of the coil element 21 that has two loop coils. This coil element 21 includes: a first loop coil 211 that has a first diameter and resonates at a first frequency f1, and a second loop coil 212 that has a second diameter and resonates at a second frequency f2 higher than the first frequency f1.

The first loop coil 211 and the second loop coil 212 are arranged in the same plane, and the entirety or at least part of the second loop coil 212 is disposed inside the circle formed by the first loop coil 211.

The first loop coil 211 and the second loop coil 212 are separately provided with feeding points, i.e., the first loop coil 211 has a first feeding point 213 and the second loop coil 212 has a second feeding point 214. The first loop coil 211 and the second loop coil 212 are respectively connected from the first feeding point 213 and the second feeding point 214 to the receiving circuit 54 of the MRI apparatus 1 via two electric supply lines, for example, two coaxial cables 215.

As shown in FIG. 5A, it is preferred that the first feeding point 213 and the second feeding point 214 are spatially separated from each other by 90 degrees within the same plane so as to achieve sufficient decoupling between the first loop coil 211 and the second loop coil 212.

To be more specific, the length of the circumference of each loop coil is usually set to be the same as the wavelength of the magnetic resonance signal or an integer multiple of this wavelength. In this case, by providing the two feeding points at positions spatially separated by 90 degrees in the same plane, when the signal amplitude at one of the two feeding points is an antinode, the signal amplitude at the other feeding point becomes a node, which can enhance the decoupling effect.

Figure 5B:
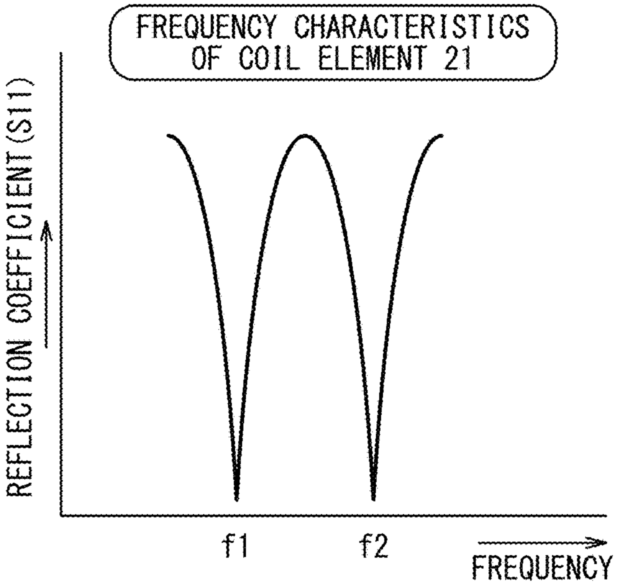
FIG. 5B is a schematic diagram illustrating frequency characteristics of the coil element according to the first embodiment.

FIG. 5B is a schematic diagram illustrating the frequency characteristics of the coil element 21 according to the first embodiment. In FIG. 5B, the horizontal axis indicates the frequency and the vertical axis indicates the reflection coefficient (i.e., S11 parameter). A smaller reflection coefficient (S11 parameter) means higher receiving sensitivity of the coil element 21 as an antenna.

As shown in FIG. 5B, the coil element 21 resonates at two frequencies, i.e., the first frequency f1 and the second frequency f2, and thus, the reflection coefficient (S11 parameter) is minimized at these two frequencies f1 and f2. As a result, the frequency characteristics of the coil element 21 are broadened as compared with the conventional coil element that includes only one loop coil.

Figure 6A:
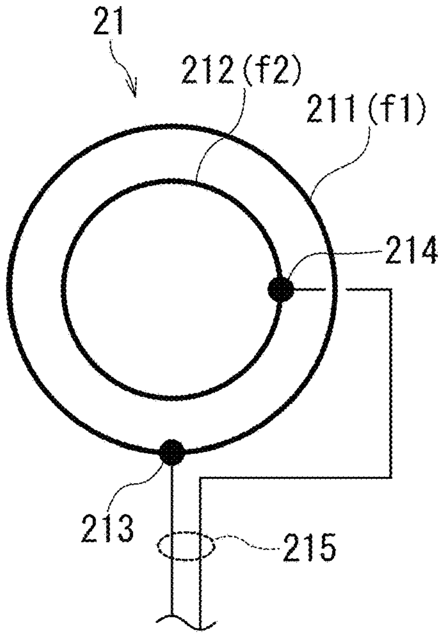
FIG. 6A is a schematic diagram illustrating the configuration of the coil element according to the first embodiment.
Figure 6B:
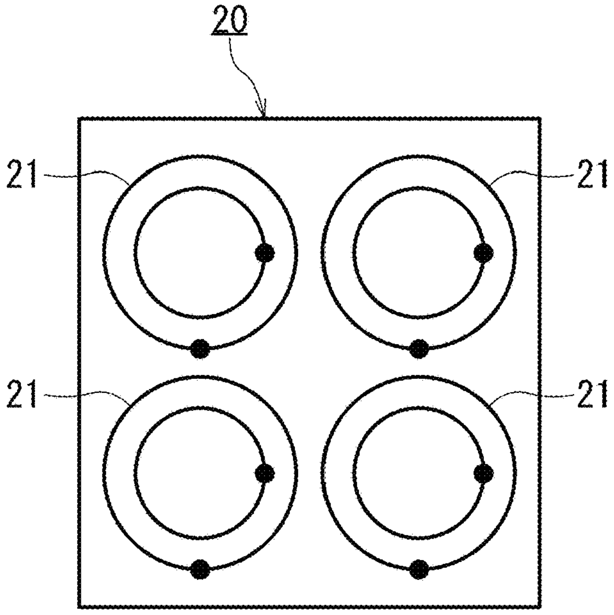
FIG. 6B is a configuration diagram illustrating a receiving coil in which coil elements according to the first embodiment are arranged in a planar array.

FIG. 6B is a configuration diagram illustrating a receiving coil 20 that is configured as an array coil by, for example, squarely arranging four coil elements 21 (FIG. 6A) of the first embodiment in a planar array (i.e., arranging the coil elements 21 in a planar array of two rows and two columns).

Modification of First Embodiment

Figure 7A:
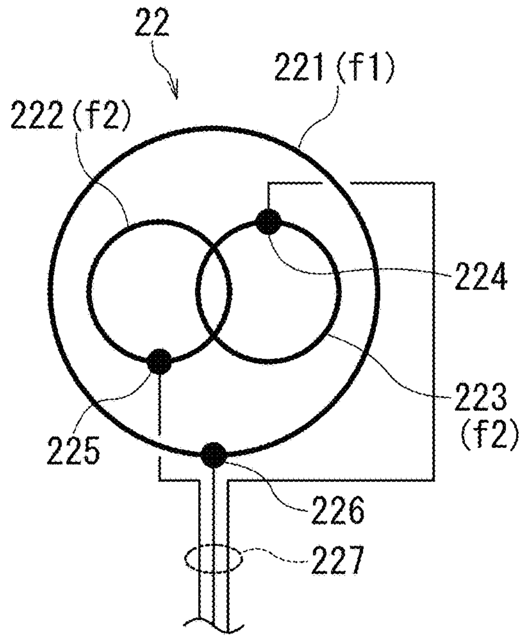
FIG. 7A is a configuration diagram illustrating a coil element according to a modification of the first embodiment.
Figure 7B:
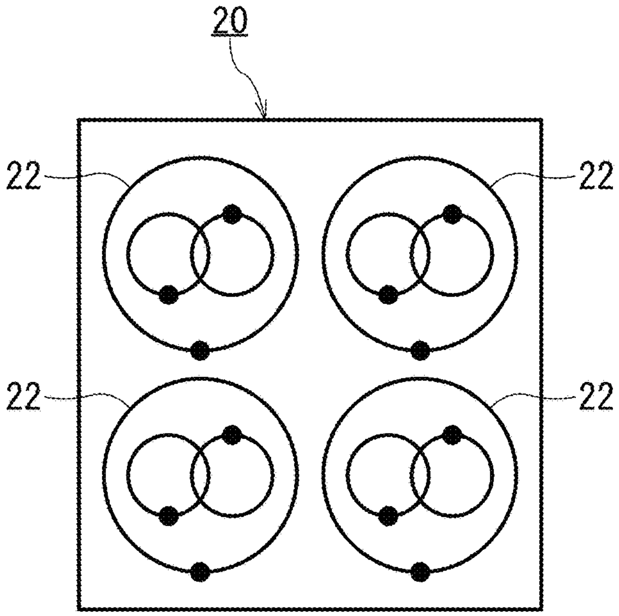
FIG. 7B is a configuration diagram illustrating a receiving coil in which the coil elements according to the modification of the first embodiment are arranged in a planar array.

FIG. 7A is a configuration diagram illustrating a coil element 22 according to a modification of the first embodiment. FIG. 7B is a configuration diagram illustrating the receiving coil 20 that is configured as an array coil by arranging the coil elements 22 in a planar array of, for example, two rows and two columns.

The coil element 22 according to the modification of the first embodiment includes: one first loop coil 221 that has the first diameter and resonates at the first frequency f1; and two second loop coils 222 and 223 that are arranged in the same plane as the first loop coil 221 and have a second diameter so as to resonate at the second frequency f2 higher than the first frequency f1. As shown in FIG. 7A, the two second loop coils 222 and 223 are arranged inside the circle formed by the first loop coil 221 in a manner that the two second loop coils 222 and 223 partially overlap each other.

The first loop coil 221 has a first feeding point 226. The second loop coils 222 and 223 respectively have second feeding points 224 and 225. The first and second loop coils 221 to 223 are connected from the respective feeding points 224 to 226 to the receiving circuit 54 of the MRI apparatus 1 via three electric supply lines, for example, three coaxial cables 227.

Second Embodiment

Figure 8A:
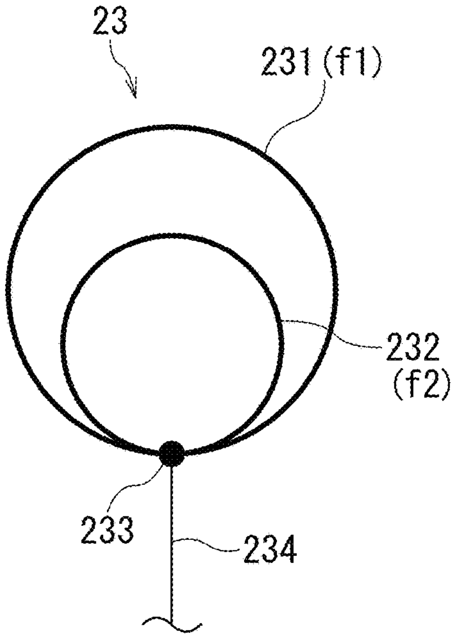
FIG. 8A is a configuration diagram illustrating a coil element according to the second embodiment.
Figure 8B:
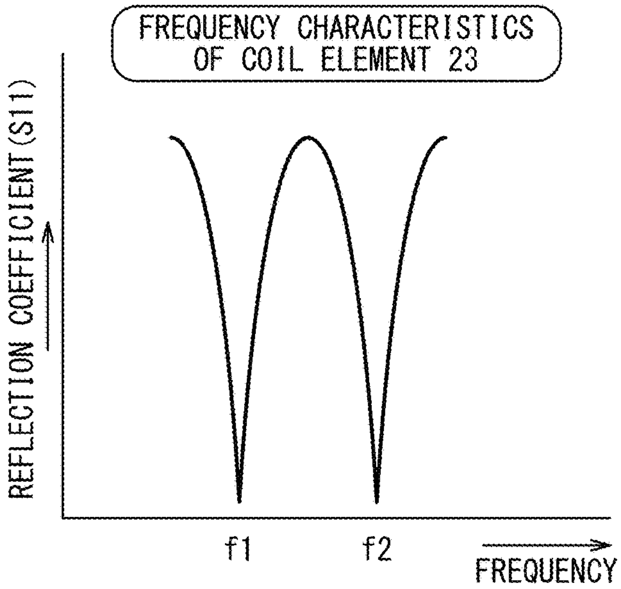
FIG. 8B is a schematic diagram illustrating frequency characteristics of the coil element according to the second embodiment.

FIG. 8A is a configuration diagram illustrating a coil element 23 according to the second embodiment. FIG. 8B is a schematic diagram illustrating the frequency characteristics of the coil element 23. The coil element 23 of the second embodiment is configured by arranging a plurality of loop coils, which are different in diameter and resonate at a plurality of different frequencies, in a single plane, similarly to the first embodiment. However, the plurality of loop coils in the second embodiment differ from the first embodiment in that power is supplied from a single feeding point.

FIG. 8A particularly illustrates the configuration of the coil element 23 when the number of loop coils is two. The coil element 23 includes: an annular first loop coil 231 that has the first diameter and resonates at the first frequency f1; and an annular second loop coil 232 that has the second diameter, is disposed in the same plane as the first loop coil 231, and resonates at the second frequency f2 higher than the first frequency f1. The annular second loop coil 232 is disposed so as to contact a circle formed by the annular first loop coil 231 from the inside at a single feeding point 233. In other words, the annular second loop coil 232 is disposed so as to be inscribed in the circle formed by the annular first loop coil 231 at a single feeding point 233. Further, from the feeding point 233, the first loop coil 231 and the second loop coil 232 are connected to the receiving circuit 54 of the MRI apparatus 1 via, for example, a single coaxial cable 234.

Reducing the number of feeding points to one allows the number of cables connected from the coil element 23 to the receiving circuit 54 to be one. As a result, the receiving coil 20 can be reduced in weight and cost.

Since the coil element 23 of the second embodiment also resonates at two frequencies of the first frequency f1 and the second frequency f2, the reflection coefficient (S11 parameter) is minimized at these two frequencies f1 and f2 as shown in FIG. 8B, and thus, the frequency characteristics of the coil element 23 have a broader band than the conventional coil element that includes only one loop coil.

Figure 9A:
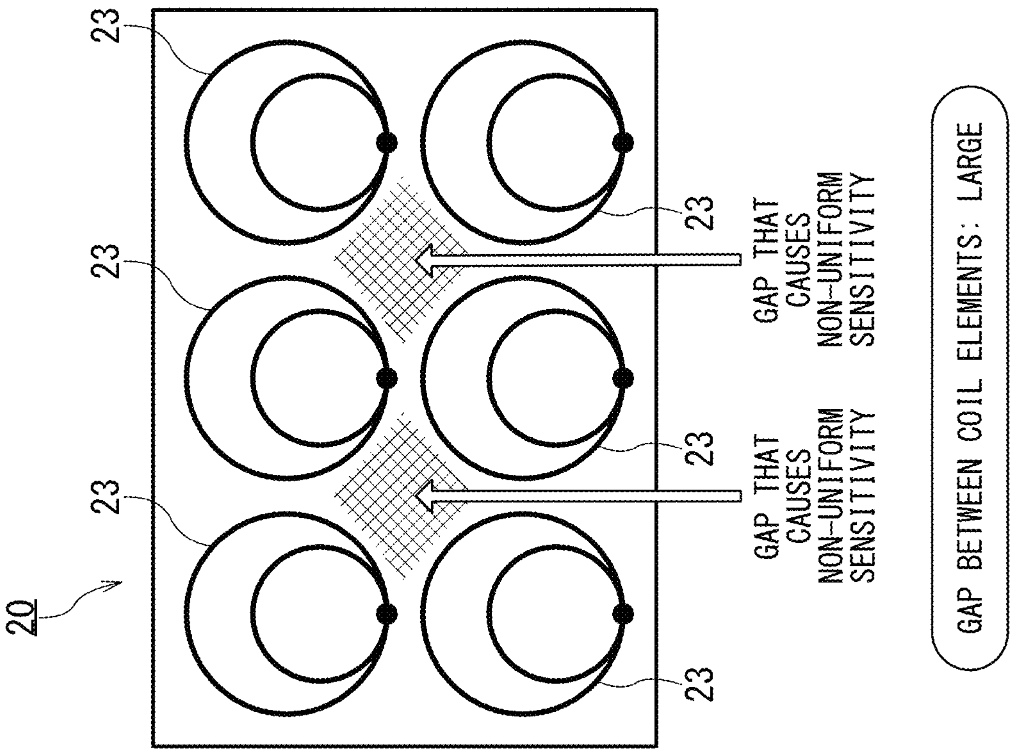
FIG. 9A is a configuration diagram illustrating a receiving coil in which annular coil elements according to the second embodiment are arranged in a planar array.

FIG. 9A is a configuration diagram illustrating the receiving coil 20 that is configured as an array coil by arranging the coil elements 23 (FIG. 8A) according to the second embodiment in a planar array of, for example, two rows and three columns.

Modification of Second Embodiment

As can be seen from FIG. 9A, in the receiving coil 20 in which the coil elements 23 of the second embodiment are arranged, there are gaps between the adjacent coil elements 23, and these gaps can be a factor of causing non-uniformity in sensitivity of the receiving coil 20.

Figure 9B:
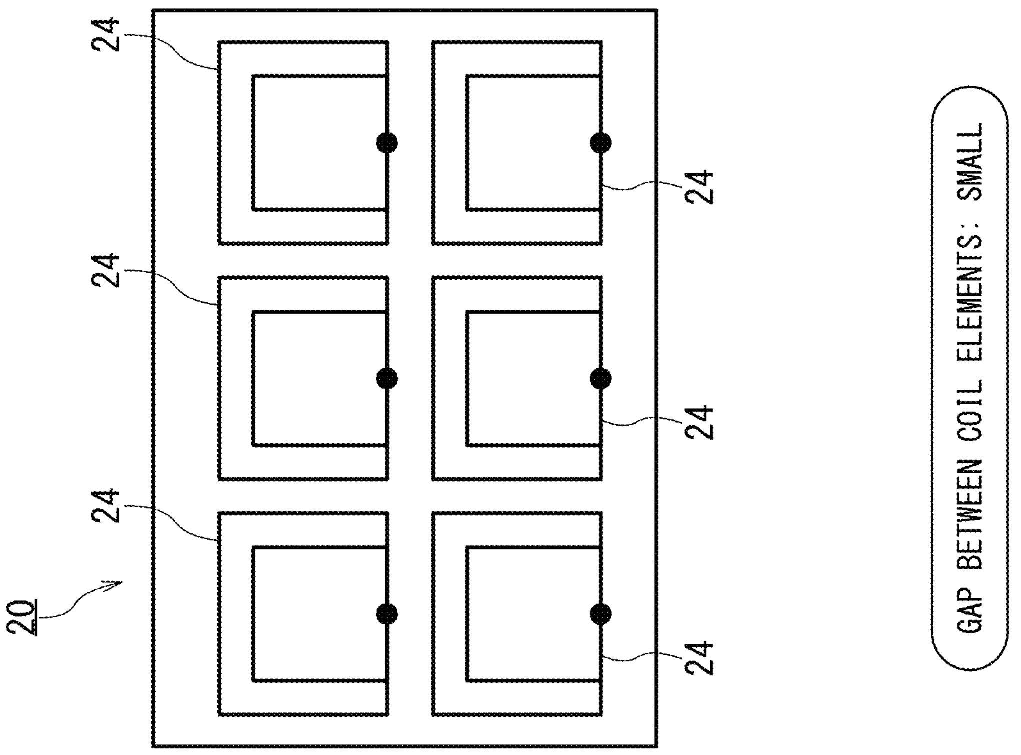
FIG. 9B is a configuration diagram illustrating a receiving coil in which rectangular coil elements according to a modification of the second embodiment are arranged in a planar array.

In order to avoid occurrence of such non-uniformity in sensitivity, in each of the coil elements 24 according to the modification of the second embodiment as shown in FIG. 9B, both the first loop coil and the second loop coil are formed in a rectangular shape. Specifically, each coil element 24 includes: a rectangular first loop coil that resonates at the first frequency; and a rectangular second loop coil that resonates at the second frequency higher than the first frequency and is disposed in the same plane as the first loop coil and inside the rectangle formed by the first loop coil.

Since the receiving coil 20 is configured as an array coil in which a plurality of such coil elements 24 are arranged in the single plane, the plurality of rectangular coil elements 24 can be close to each other with a smaller gap in this array coil. Since the gap between the adjacent coil elements 24 is reduced, non-uniformity in sensitivity of the receiving coil 20 can be suppressed.

Third Embodiment

Figure 10A:
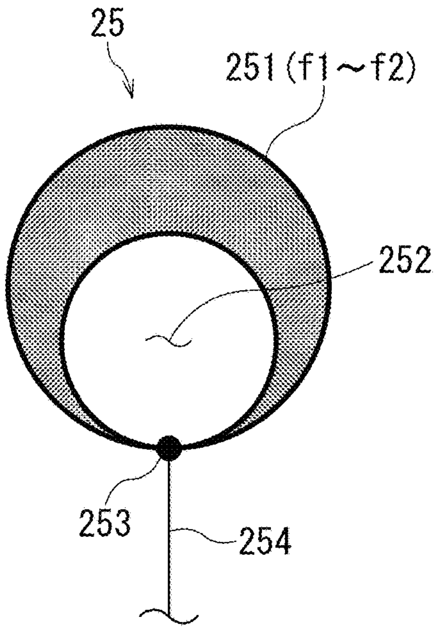
FIG. 10A is a configuration diagram illustrating a coil element according to the third embodiment.

FIG. 10A is a configuration diagram illustrating a coil element 25 according to the third embodiment. The coil element 25 according to the third embodiment is a broadband coil made of a conductor plate having a predetermined shape in which an opening of a predetermined shape is formed. In this coil element 25, the lower limit frequency of the bandwidth is determined by the length of the outer circumference of the conductor plate, and the upper limit frequency of the bandwidth is determined by the length of the inner circumference of the conductor plate (i.e., by the length of the outer circumference of the opening).

The conductor plate and the opening are not limited to specific shapes but may be formed into various shapes such as a rectangular shape, a polygonal shape, an elliptical shape, and a circular shape. FIG. 10A illustrates the coil element 25 when both the conductor plate and the opening have a circular shape.

As shown in FIG. 10A, the coil element 25 is composed of a conductor plate 251 in which an opening 252 is formed. The outer circumference shape of the conductor plate 251 is a first circle having a first diameter, and the outer circumference shape of the opening 252 is a second circle having a second diameter smaller than the first diameter. The opening 252 is formed such that the second circle contacts the first circle from the inside, and a feeding point 253 is provided at the point where the second circle contacts the first circle.

One cable 254 (for example, one coaxial cable 254) is connected to the feeding point 253 for transmitting the received MR signal to the receiving circuit 54.

Figure 10B:
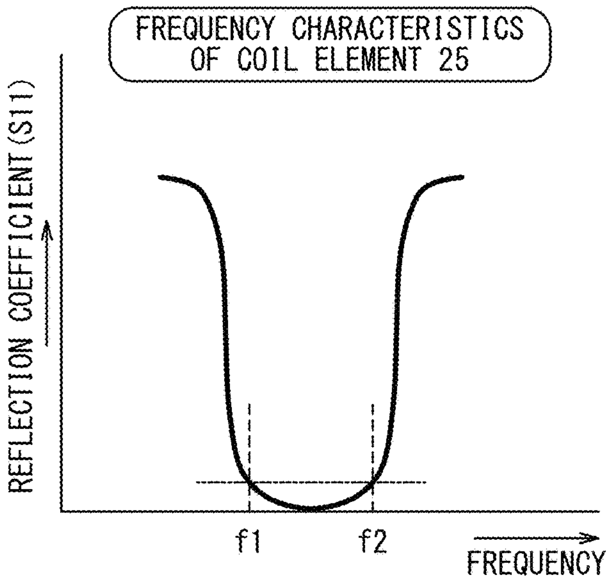
FIG. 10B is a schematic diagram illustrating frequency characteristics of the coil element according to the third embodiment.

FIG. 10B is a schematic diagram illustrating the frequency characteristics of the coil element 25. As described above, in the coil element 25 of the third embodiment, the lower limit frequency of the bandwidth is determined by the length of the outer circumference of the conductor plate, and the upper limit frequency of the bandwidth is determined by the length of the inner circumference of the conductor plate (i.e., outer circumference of the opening). In the case of the shape shown in FIG. 10A, the frequency characteristics of the coil element 25 show broadband characteristics represented by: the lower limit frequency f1 determined by the circumferential length of the conductor plate 251; and the upper limit frequency f2 determined by the circumferential length of the opening 252.

Modification of Third Embodiment

Figure 11A:
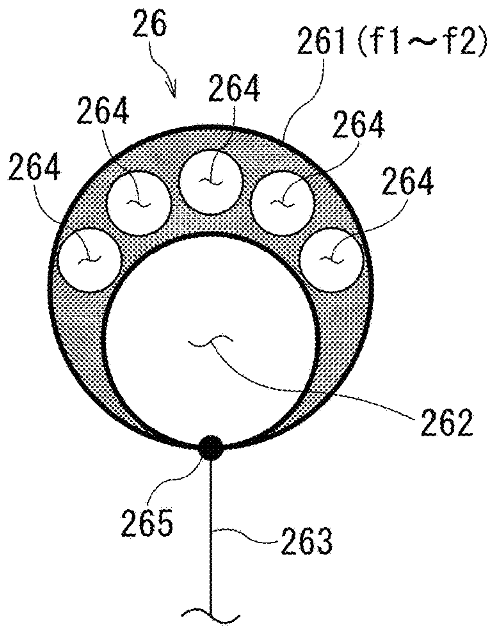
FIG. 11A is a configuration diagram illustrating a coil element according to a first modification of the third embodiment.

FIG. 11A is a configuration diagram illustrating a coil element 26 according to a first modification of the third embodiment. As shown in FIG. 11A, the coil element 26 of the first modification of the third embodiment has a circular conductor plate 261 and a circular opening 262, similarly to the coil element 25 of the third embodiment. Thus, the coil element 26 of the first modification also shows broadband characteristics represented by: the lower limit frequency f1 determined by the circumferential length of the conductor plate 261; and the upper limit frequency f2 determined by the circumferential length of the opening 262.

In the coil element 26 of the first modification of the third embodiment, the conductor plate 261 is provided with a plurality of smaller openings 264 around the opening 262. These smaller openings 264 can suppress the phenomenon that the magnetic flux of the static magnetic field, which is applied in the direction of penetrating the conductor plate 261, is disturbed by the influence of the conductor plate 261. In addition, the plurality of the smaller openings 264 can also suppress the phenomenon that the distribution of the RF magnetic field of the transmitting pulse generated by the transmitting coil 62 is disturbed by the influence of the conductor plate 261. Note that, similarly to the third embodiment, one coaxial cable 263, for example, is connected to one feeding point 265, and the coaxial cable 263 transmits the received MR signal to the receiving circuit 54.

Figure 11B:
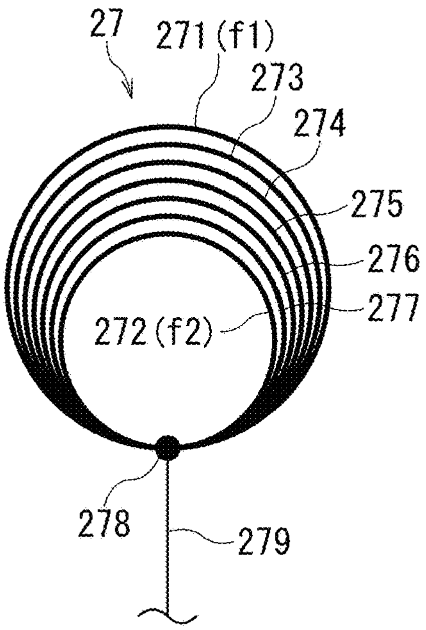
FIG. 11B is a configuration diagram illustrating a coil element according to a second modification of the third embodiment.

FIG. 11B is a configuration diagram illustrating a coil element 27 according to a second modification of the third embodiment. As shown in FIG. 11B, the coil element 27 of the second modification of the third embodiment is configured by arranging a plurality of loop coils, which are different in diameter and resonate at respective different frequencies, in a single plane. The second modification can be interpreted as a combination of the coil element 23 (FIG. 8A) according to the second embodiment and the coil element 25 (FIG. 10A) according to the third embodiment. In the coil element 27 of the second modification of the third embodiment shown in FIG. 11B, for example, seven loop coils 271 to 277, which are different in diameter from each other, are arranged so as to contact each other at one feeding point 278. From this feeding point 278, the received MR signals are transmitted to the receiving circuit 54 via, for example, one coaxial cable 279.

This coil element 27 shows broadband characteristics represented by: the lower limit frequency f1 determined by the circumferential length of the outermost loop coil 271; and the upper limit frequency f2 determined by the circumferential length of the innermost loop coil 277.

Figure 12C:
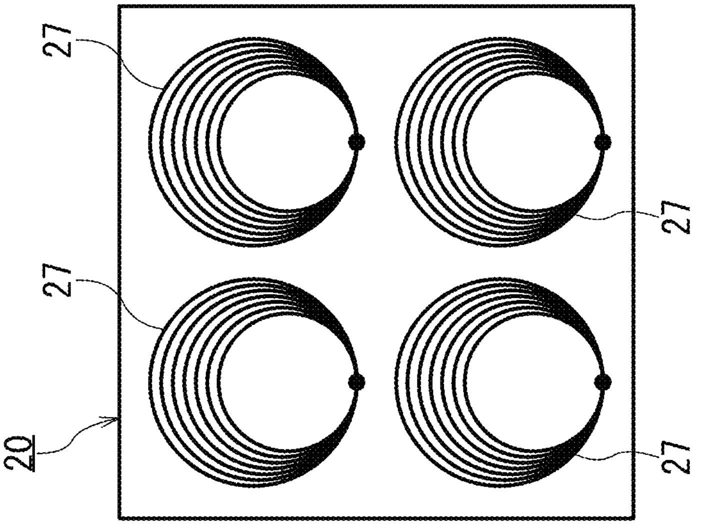
FIG. 12C is a configuration diagram illustrating a receiving coil in which the coil elements according to the second modification of the third embodiment are arranged in a planar array.
Figure 12B:
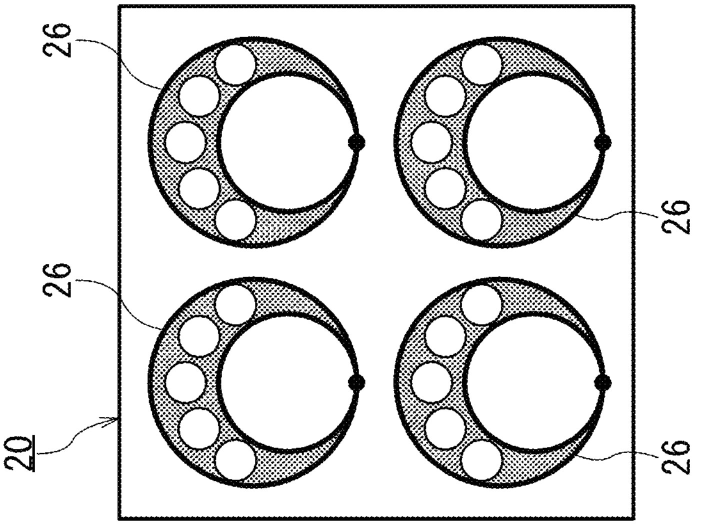
FIG. 12B is a configuration diagram illustrating a receiving coil in which the coil elements according to the first modification of the third embodiment are arranged in a planar array.
Figure 12A:
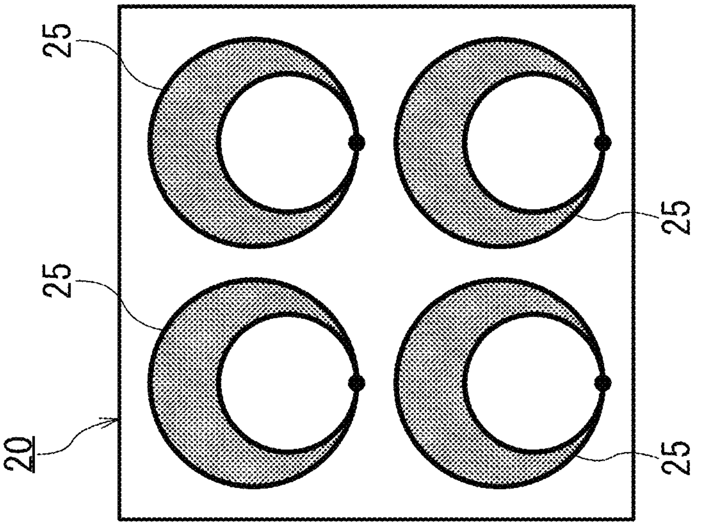
FIG. 12A is a configuration diagram illustrating a receiving coil in which the coil elements according to the third embodiment are arranged in a planar array.

FIG. 12A illustrates a receiving coil 20 in which a plurality of coil elements 25 according to the third embodiment are arranged in a planar array. FIG. 12B illustrates a receiving coil 20 in which a plurality of coil elements 26 according to the first modification of the third embodiment are arranged in a planar array. FIG. 12C illustrates a receiving coil 20 in which a plurality of coil elements 27 according to the second modification of the third embodiment are arranged in a planar array. Although the number of the coil elements 25, 26, or 27 is four in each of FIG. 12A to FIG. 12C, the number of the coil elements is not limited to the illustrated embodiments.

Fourth Embodiment

Figure 13A:
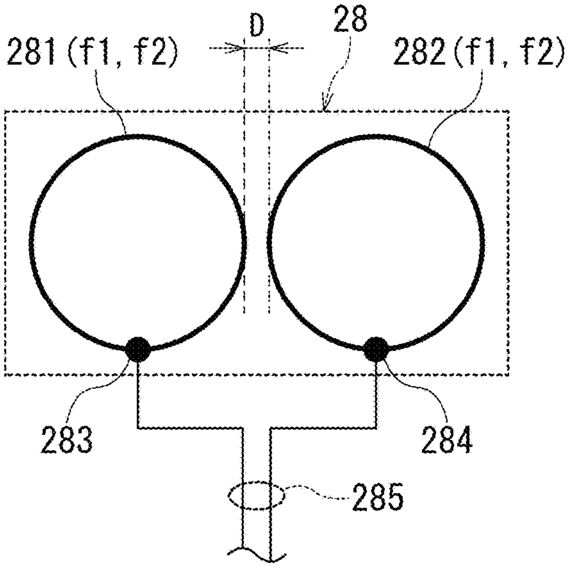
FIG. 13A is a configuration diagram illustrating a coil element according to the fourth embodiment.

FIG. 13A is a configuration diagram illustrating a coil element 28 according to the fourth embodiment. The coil element 28 of the fourth embodiment is composed of a pair of sub-coil elements 281 and 282 that are the same in diameter. The two sub-coil elements 281 and 282 are closely arranged in a single plane with a predetermined distance D so as not to overlap each other. The sub-coil element 281 has a feeding point 283 and the sub-coil element 282 has a feeding point 284. The two sub-coil elements 281 and 282 are connected to the receiving circuit 54 via two cables 285 that are connected to respective feeding points 283 and 284.

Figure 13B:
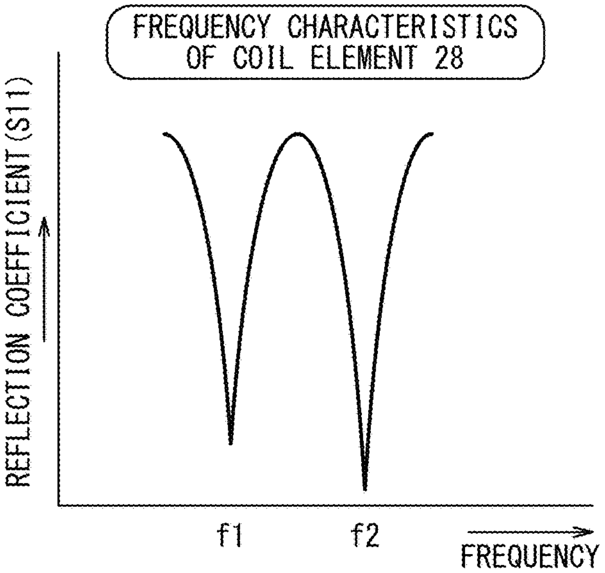
FIG. 13B is a schematic diagram illustrating frequency characteristics of the coil element according to the fourth embodiment.

FIG. 13B is a schematic diagram illustrating the frequency characteristics of the coil element 28 according to the fourth embodiment. Each of the two sub-coil elements has the first resonance frequency f1 and the second resonance frequency f2 higher than the first resonance frequency f1.

As shown in FIG. 13A, in the case where two loop coils with the same diameter are arranged side by side such that their coil surfaces are on the same plane, the following phenomenon is known. That is, when the distance D between the two sub-coil elements is appropriately adjusted, frequency characteristics where, instead of one resonance frequency, a plurality of resonance frequencies can be obtained due to the coupling effect between the two sub-coil elements. Such phenomenon is utilized by the coil element 28 of the fourth embodiment, and the frequency characteristics of the coil element 28 can be adjusted by changing the distance D between the two sub-coil elements. For example, the frequency characteristics having two resonance points as shown in FIG. 13B can be obtained.

Further, when the distance D between the two sub-coil elements is appropriately adjusted, the reflection coefficient (S11) at the first resonance frequency f1 and the reflection coefficient (S11) at the second resonance frequency f2 can be set to different values. In this case, distance D is preferably adjusted in such a manner that the second S11 parameter corresponding to the higher frequency (i.e., second resonance frequency f2) is smaller than the first S11 parameter corresponding to the lower frequency (i.e., first resonance frequency f1).

This is because the magnetic resonance frequency is higher in the region closer to the magnet 10 than in the region farther from the magnet 10, whereas the region closer to the magnet 10 is farther from the receiving coil 20 (FIG. 4). Thus, in terms of sensitivity of the receiving coil 20, it is preferred that the sensitivity of the region closer to the magnet 10 (i.e., region where the magnetic resonance frequency is high) is set higher than the sensitivity of the region farther from the magnet 10 (i.e., region where the magnetic resonance frequency is low). In other words, the reflection coefficient (S11) in the region near the magnet 10 (i.e., region where the magnetic resonance frequency is high) is desirably smaller than the reflection coefficient (S11) in the region far from the magnet 10 (i.e., region where the magnetic resonance frequency is low).

Figure 14:
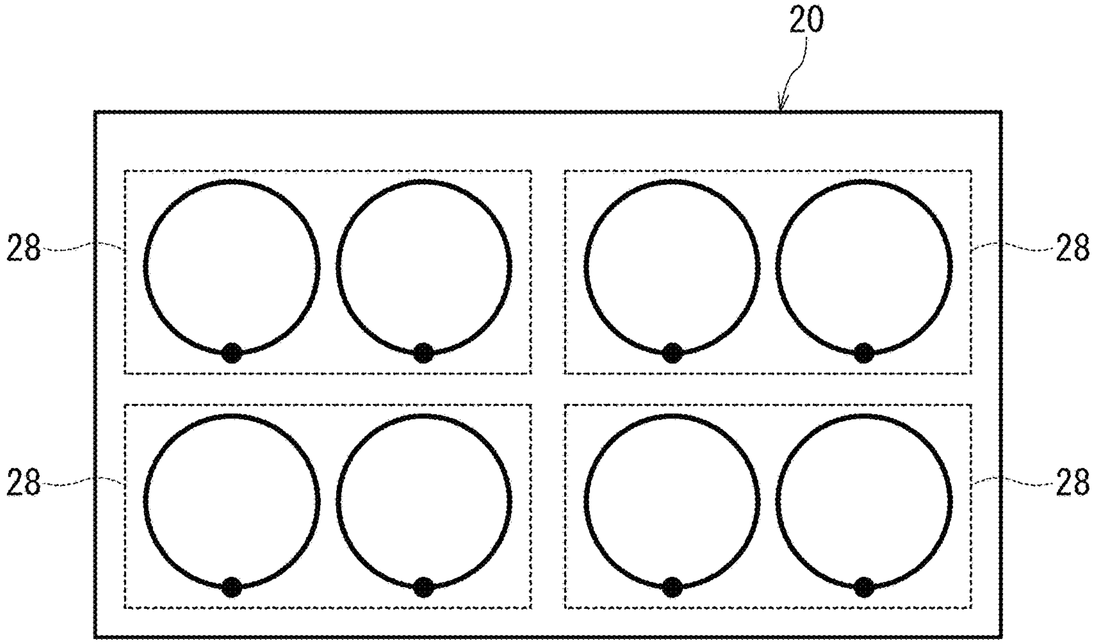
FIG. 14 is a configuration diagram illustrating a receiving coil in which the coil elements according to the fourth embodiment are arranged in a planar array.

FIG. 14 is a configuration diagram illustrating a receiving coil 20 that is configured as an array coil by arranging a plurality of coil elements 28 (four coil elements 28 in the case of FIG. 14) according to the fourth embodiment in a single plane.

According to at least one embodiment described above, in a receiving coil for receiving an MR signal, a wide FOV can be ensured by simultaneously receiving the MR signal having a plurality of different magnetic resonance frequencies, or by receiving the MR signal having a broad frequency band.

While certain embodiments have been described, these embodiments have been presented by way of example only, and are not intended to limit the scope of the invention. Indeed, the novel methods and systems described herein may be embodied in a variety of other forms; furthermore, various omissions, substitutions and changes in the form of the methods and systems described herein may be made without departing from the scope of the invention as defined by the appended claims.

What is claimed is:

1. A receiving coil, comprising:
at least one coil element that can simultaneously receive a magnetic resonance (MR) signal having a plurality of different frequencies, wherein:
a resonance structure for the plurality of different frequencies is provided disposed in a single plane in the at least one coil element,
the at least one coil element of the receiving coil is configured to receive the MR signal emitted from an object in response to an excitation pulse applied to the object, the object being placed in a static magnetic field; and
the MR signal has the plurality of different frequencies depending on a position of the object in the static magnetic field having a non-uniform static magnetic field distribution.

2. The receiving coil according to claim 1, wherein the receiving coil is configured as an array coil in which a plurality of the coil elements are arranged in the single plane.

3. The receiving coil according to claim 1, wherein the at least one coil element is configured as a plurality of loop coils that are arranged in the single plane.

4. The receiving coil according to claim 3, wherein
the plurality of loop coils are different in diameter, and are supplied with power from the respective different feeding points, and
each of the plurality of loop coils resonates at each of the plurality of different frequencies.

5. The receiving coil according to claim 4, wherein
the at least one coil element includes a first loop coil having a first diameter and resonating at a first frequency and a second loop coil having a second diameter and resonating at a second frequency higher than the first frequency, and
the second loop coil is disposed in a same plane as the first loop coil, and an entirety or at least a part of the second loop coil is disposed inside a circle formed by the first loop coil.

6. The receiving coil according to claim 5, wherein a first feeding point of the first loop coil and a second feeding point of the second loop coil are provided in the same plane at positions spatially separated from each other by 90 degrees.

7. The receiving coil according to claim 4, wherein
the at least one coil element includes one first loop coil having a first diameter and resonating at a first frequency, and two second loop coils, each of which has a second diameter and resonates at a second frequency higher than the first frequency, and
the two second loop coils are arranged inside a circle formed by the first loop coil and in a same plane as the first loop coil, in such a manner that the two second loop coils partially overlap each other.

8. The receiving coil according to claim 3, wherein
the plurality of loop coils are different in diameter, and are supplied with power from a single feeding point in common, and
each of the plurality of loop coils resonates at each of the plurality of different frequencies.

9. The receiving coil according to claim 8, wherein
the at least one coil element includes an annular first loop coil having a first diameter and resonating at a first frequency, and an annular second loop coil having a second diameter and resonating at a second frequency higher than the first frequency, and
the annular second loop coil is disposed in a same plane as the annular first loop coil in such a manner that the annular second loop coil contacts a circle formed by the annular first loop coil from an inside at the single feeding point.

10. The receiving coil according to claim 8, wherein
the at least one coil element includes a rectangular first loop coil resonating at a first frequency, and a rectangular second loop coil being disposed in a same plane as the first loop coil and resonating at a second frequency higher than the first frequency,
the second loop coil is disposed inside a rectangle formed by the first loop coil,
the receiving coil is configured as an array coil in which a plurality of the coil elements are arranged in the single plane, and
the plurality of the coil elements are densely arranged in the array coil so as to be close to each other but without overlapping.

11. The receiving coil according to claim 8, further comprising:
a filter configured to separate each of the plurality of different frequencies, and
a cable that is connected to the feeding point at one end and is connected to the filter at another end.

12. An MRI apparatus comprising the receiving coil according to claim 1.

13. A receiving coil, comprising:
at least one coil element that can simultaneously receive a magnetic resonance signal having a plurality of different frequencies, wherein
a resonance structure for the plurality of different frequencies is disposed in a single plane in the at least one coil element,
the at least one coil element is configured as a broadband coil that is made of a conductor plate of a predetermined shape having an opening of a predetermined shape,
a lower limit frequency of bandwidth of the broadband coil is determined by an outer circumferential length of the conductor plate, and
an upper limit frequency of the bandwidth of the broad band coil is determined by an inner circumferential length of the conductor plate.

14. The receiving coil according to claim 13, wherein
an outer circumferential shape of the conductor plate is a first circle having a first diameter,
an outer circumferential shape of the opening is a second circle having a second diameter smaller than the first diameter,
the opening is formed in such a manner that the second circle contacts the first circle from the inside at a point, and
a feeding point is provided at the point where the second circle contacts the first circle.

15. The receiving coil according to claim 13, wherein a plurality of smaller openings are provided in the conductor plate around the opening.

16. The receiving coil according to claim 13, further comprising:
a filter configured to separate each of the plurality of different frequencies, and
a cable that is connected to a feeding point at one end and is connected to the filter at another end.

17. A receiving coil, comprising:

at least one coil element that can simultaneously receive a magnetic resonance signal having a plurality of different frequencies, wherein a resonance structure for the plurality of different frequencies is disposed in a single plane in the at least one coil element, the at least one coil element is configured as a pair of sub-coil elements that have a same diameter and are disposed in the single plane with a predetermined distance so as not to overlap each other, and each of the pair of sub-coil elements is separately provided with a feeding point and resonates at a first resonance frequency and a second resonance frequency higher than the first resonance frequency.

18. The receiving coil according to claim 17, wherein each of the pair of sub-coil elements is configured to adjust frequency characteristics including the first resonance frequency and the second resonance frequency by changing the predetermined distance between the pair of sub-coil elements.

19. The receiving coil according to claim 17, wherein the predetermined distance is adjusted in such a manner that a second S11 parameter corresponding to the second resonance frequency is smaller than a first S11 parameter corresponding to the first resonance frequency.

20. The receiving coil according to claim 18, wherein the predetermined distance is adjusted in such a manner that a second S11 parameter corresponding to the second resonance frequency is smaller than a first S11 parameter corresponding to the first resonance frequency.

* * * * *